United States Patent
Wolf et al.

(10) Patent No.: US 12,173,312 B1
(45) Date of Patent: Dec. 24, 2024

(54) METHOD FOR IN VITRO FERTILIZATION IN A BIOREACTOR

(71) Applicants: David A. Wolf, Houston, TX (US);
Alvin T. Rockhill, Akron, OH (US);
William H. Beeson, Carmel, IN (US);
Tammy Wolf, Houston, TX (US)

(72) Inventors: David A. Wolf, Houston, TX (US);
Alvin T. Rockhill, Akron, OH (US);
William H. Beeson, Carmel, IN (US);
Tammy Wolf, Houston, TX (US)

( * ) Notice: Subject to any disclaimer, the term of this patent is extended or adjusted under 35 U.S.C. 154(b) by 912 days.

(21) Appl. No.: 16/820,101

(22) Filed: Mar. 16, 2020

Related U.S. Application Data (60) Provisional application No. 62/819,990, filed on Mar. 18, 2019.

(51) Int. Cl.
*C12N 5/075* (2010.01)
*C12M 3/00* (2006.01)

(52) U.S. Cl.
CPC ........... *C12N 5/0609* (2013.01); *C12M 21/06* (2013.01); *C12N 2500/32* (2013.01); *C12N 2501/01* (2013.01)

(58) Field of Classification Search
None
See application file for complete search history.

(56) References Cited

U.S. PATENT DOCUMENTS

| | | | |
|---|---|---|---|
| 4,988,623 A | 1/1991 | Schwarz et al. | |
| 5,026,650 A | 6/1991 | Schwarz et al. | |
| 5,153,131 A | 10/1992 | Wolf et al. | |
| 5,155,034 A | 10/1992 | Wolf et al. | |
| 5,945,338 A * | 8/1999 | Spaulding | C12M 27/10 435/298.2 |
| 6,001,643 A * | 12/1999 | Spaulding | C12M 23/34 435/304.2 |
| 6,130,086 A * | 10/2000 | Nakazawa | A01K 67/027 435/325 |
| 6,352,997 B1 | 3/2002 | Waldstreicher et al. | |
| 6,838,235 B2 | 1/2005 | Gardner et al. | |
| 7,456,019 B2 * | 11/2008 | Goodwin | C12N 5/0062 435/173.1 |
| 2011/0207225 A1 * | 8/2011 | Mehta | C12N 13/00 435/173.6 |
| 2014/0242581 A1 * | 8/2014 | Johnson | C12Q 1/6883 435/6.11 |

OTHER PUBLICATIONS

Elder, K. (2001). In vitro fertilization. Preimplantation Genetic Diagnosis, 53-78. (Year: 2001).*
Kitaji, H., Ookutsu, S., Sato, M., & Miyoshi, K. (2015). A new rolling culture-based in vitro fertilization system capable of reducing polyspermy in porcine oocytes. Animal Science Journal, 86(5), 494-498. (Year: 2015).*
Koike, T., et al. (2010). In-vitro culture with a tilting device in chemically defined media during meiotic maturation and early development improves the quality of blastocysts derived from in-vitro matured and fertilized porcine oocytes. Journal of Reproduction and Development, 1006110281-1006110281. (Year: 2010).*
Kojima et al. Effects of Simulated Microgravity on Mammalian Fertilization and Preimplantation Embryonic Development In Vitro. Fertility and Sterility, 2000. 74(6):1142-1147.*
Ito et al., Effects of Centrifugal Gravity on the Fertilization and Early Development of Mammals. Journal of Mammalian Ova Research, 2000. 17:84-89.*

\* cited by examiner

*Primary Examiner* — Christopher M Babic
*Assistant Examiner* — Kimberly A Aron
(74) *Attorney, Agent, or Firm* — Alvin T. Rockhill (57) ABSTRACT

A highly effective technique for fertilizing an oocyte with a sperm cell to produce a zygote can be carried out in a bioreactor and the zygote can optionally be cultured in the bioreactor into a blastocyst stage embryo for implantation into the uterus of a female recipient. The success rate and probability of fertilization is enhanced by operating the bioreactor reactor under conditions of inter-galactic motion which increases the probability of the sperm coming in close proximity to and fertilizing the oocyte. This method involves the steps of collecting an oocyte from a female donor, collecting sperm from a male donor, fertilizing the oocyte with the sperm in a rotating bioreactor to produce a zygote, culturing the zygote into a blastocyst stage embryo, and implanting the blastocyst stage embryo into a uterus of a recipient female.

18 Claims, 5 Drawing Sheets

METHOD FOR IN VITRO FERTILIZATION IN A BIOREACTOR

This application claims benefit of U.S. Provisional Patent Application Ser. No. 62/819,990, filed on Mar. 18, 2019. The teachings of U.S. Provisional Patent Application Ser. No. 62/819,990 are incorporated herein by reference in their entirety.

FIELD OF THE INVENTION

The present invention relates to the utilization of a bioreactor during the fertilization and early embryonic development stages of in vitro fertilization. The techniques of this invention are applicable for use with respect to humans and many animals.

BACKGROUND OF THE INVENTION

In vitro fertilization (IVF) is a process wherein an egg is fertilized with sperm outside the body or in vitro ("in glass"). The in vitro fertilization procedure involves monitoring and stimulating the ovulatory process of a female, removing an ovum or ova (egg or eggs) from the ovaries and subsequently exposing them to sperm for fertilization in a liquid medium outside of the body. After the fertilized egg (the zygote) is allowed to mature in an embryonic culture for a period of about 2 to about 6 days, it is implanted in the uterus of the same or another woman with the intention of establishing a successful pregnancy.

IVF is a type of assisted reproductive technology used for infertility treatment and gestational surrogacy. A fertilized egg may be implanted into the uterus of a surrogate in which case the resulting offspring is genetically unrelated to the surrogate. Some countries banned or otherwise regulate the availability of in vitro fertilization procedures which has giving rise to fertility tourism. In 1978 Louise Brown was the first child successfully born after her mother underwent an in vitro fertilization procedure. The procedure took place at Dr. Kershaw's Cottage Hospital (now Dr. Kershaw's Hospice) in Royton, Oldham, England. Robert G. Edwards was awarded the Nobel Prize in Physiology or Medicine in 2010 for developing the procedure. By utilizing the in vitro fertilization procedure women who are past their reproductive years, have infertile male partners, have idiopathic female-fertility issues, or have reached menopause, can still become pregnant. It has been estimated that eight million children have been born worldwide as of 2018 by the utilization of in vitro fertilization and other assisted reproduction techniques In vitro fertilization and subsequent embryo transfer comprises fertilizing ova with sperm in vitro and then transplanting the developed embryo into the uterus of a female (human or animal). In vitro fertilization seeks to duplicate, to a large extent, the conditions and processes normally occurring within the female reproductive system that are necessary for oocyte development, fertilization, and early embryonic development. In vitro fertilization, which is frequently referred to as IVF, involves several discrete laboratory or clinical procedures, including collection of the oocytes from the ovary of a female, collection and preparation of the sperm, fertilization, and, once fertilized eggs are identified, a period of early embryonic development, and then transfer of the embryo to the uterus of a recipient mother. Each of these steps can take place over extended periods of time. In fact, sperm cells can be frozen for subsequent use in fertilization years after being collected from a male donor. However, some individual cells involved in the procedure have a continuing need for nutrients and are subjected to significant stress as a result of clinical manipulation and altered environmental conditions.

During in vitro fertilization, a culture medium is ordinarily used as a substitute for the fluid secreted by the female reproductive tract that would ordinarily surround the gametes, zygote, and developing embryo. Some laboratories carrying out in vitro fertilization use a single culture medium throughout the various procedures involved. In a number of laboratories, there has been a tendency to use tissue culture media for in vitro fertilization procedures, such as Ham's F-10, which is formulated to support somatic cell growth, not gamete or embryonic cell growth. Tissue culture media generally are complicated systems, containing an array of amino acids, vitamins and other constituents. They can contain components that significantly impair embryonic development and viability after transfer.

Other laboratories have used simple culture media, consisting of balanced salt solutions supplemented with carbohydrate energy sources such as glucose, pyruvate and lactate. Earle's, T-6, and human tubal fluid (HTF) are examples of such simple culture media. These media generally lack certain key components found in the female reproductive tract, such as non-essential amino acids, and their constituents are not formulated in concentrations that meet the specific changing needs of the gametes and developing embryo at various stages of their development.

The two types of culture media commonly used for in vitro fertilization generally are only capable of supporting embryonic development to the eight-cell stage. Such media are ordinarily not capable of supporting and producing a viable blastocyst stage embryo, complete with an epithelium and competent inner cell mass. Accordingly, embryo transfer, the return of the fertilized oocyte to the uterus of the mother, usually occurs at around the four-cell stage (day two) or around the eight-cell stage (day three). This is a time when the four- or eight-cell embryo would not typically have arrived in the uterus of the mother, if fertilization had occurred in vivo. Embryo transfer at this time involves placing the cleavage stage embryo in an environment oriented to a blastocyst stage embryo. The cleavage stage embryo must then undergo further development in a non-homologous environment to reach the blastocyst stage, in which the embryo has trophectoderm cells capable of implanting in the uterine lining.

Research and human trials have led to the development of culture media, G1 and G2, which represent significant advancements in adaptation of culture media to the physiological needs of the cleavage stage embryo and the embryo in the eight-cell through blastocyst stage of development. These media are described in the following publications: Barnes, Crombie, Gardner, et al, Blastocyst Development and Birth After In-vitro Maturation of Human Primary Oocytes, Intracytoplasmic Sperm Injection and Assisted Hatching, Human Reproduction, vol. 10, no. 12, pp. 3243-47 (December 1995); Gardner and Lane, Culture and Selection of Viable Blastocysts: A Feasible Proposition for Human IVF?, Human Reproduction Update, Vol. 3, No. 4, pp. 367-82 (1997); Gardner, Vella, Lane, et al, Culture and Transfer of Human Blastocysts Increases Implantation Rates and Reduces the Need for Multiple Embryo Transfers, Fertility and Sterility, Vol. 69, No. 1, pp. 84-88 (January 1998). Use of these media, and particularly the G2 medium, supports the growth and development of viable blastocyst stage embryos in vitro. Accordingly, the development of these media paved the way for new approaches to embryo transfer to the uterus at the blastocyst stage, when the embryo is most adapted to surviving in the uterine environment and has developed structures and capabilities required for implantation to take place. Research utilizing the G1 and G2 media, and embryo transfer at the blastocyst stage, suggests that these media contribute to higher pregnancy rates, and reduces the need for transfer of multiple embryos and the risk of multiple births. Neither of these media, however, is optimized for supporting the gametes, oocyte maturation, or fertilization.

U.S. Pat. No. 6,838,235 B2 describes a method wherein instead of immersing human reproductive cells in a single culture medium throughout the various procedures used in in vitro fertilization, a process is provided by which the reproductive cells may be moved through a sequence of distinct culture media as the various in vitro fertilization procedures are carried out. In one implementation, the culture media is specifically formulated to provide a physical environment similar to that found within the female reproductive tract and is conducive to growth and development of human reproductive cells during the various stages of the in vitro fertilization procedure. In this regard, specifically formulated culture media can be applied to support the reproductive cells in one or more of the following procedures: oocyte retrieval and handling; oocyte maturation; ordinary fertilization; oocyte, zygote and embryo examination and biopsy; embryonic development to the eight-cell stage; embryonic development to the blastocyst stage; embryo transfer; and cryopreservation.

SUMMARY OF THE INVENTION

The subject invention discloses a highly effective technique for fertilizing an oocyte with a sperm cell to produce a zygote and for optionally culturing the zygote into a blastocyst stage embryo for implantation into the uterus of a female human or animal recipient. In any case, the success rate and probability of fertilization is enhanced in the bioreactor reactor under conditions of inter-galactic motion between the sperm and the oocyte which increases the probability of the sperm coming in close proximity to and fertilizing the oocyte within the in vitro fertilization medium within the reactor. The bioreactor also provides excellent conditions for culturing the zygote into a blastocyst stage embryo by virtue of providing the simultaneous conditions of (a) space collocation, (b) low hydrodynamic stress, and (c) three-dimensional special freedom. In any case, the bioreactor provides excellent conditions for culturing the embryo to attain a robust blastocyst stage embryo which is highly amenable for implantation into the uterus of a recipient female.

The subject invention more specifically discloses a method for in vitro fertilization of an oocyte which comprises fertilizing the oocyte with a sperm cell to produce a zygote, wherein the fertilization is conducted in a rotating bioreactor containing an in vitro fertilization medium. This method optionally further comprises culturing the zygote into a blastocyst stage embryo in the rotating bioreactor. The blastocyst stage embryo can then subsequently be implanting into a uterus of a recipient female resulting in pregnancy of the female.

The present invention also reveals a method for in vitro fertilization that involves the steps of collecting an oocyte from a female donor, collecting sperm from a male donor, fertilizing the oocyte with the sperm in a rotating bioreactor to produce a zygote, culturing the zygote into a blastocyst stage embryo, and implanting the blastocyst stage embryo into a uterus of a recipient female.

The subject invention also discloses a method for in vitro fertilization that involves the steps of collecting an oocyte from a female donor, collecting sperm from a male donor, fertilizing the oocyte with the sperm to produce a zygote, culturing the zygote in a rotating bioreactor into a blastocyst stage embryo, and implanting the blastocyst stage embryo into a uterus of a recipient female.

DETAILED DESCRIPTION OF THE INVENTION

In the practice of this invention oocyte is retrieved from the ovary of a donor female (human or animal). This is typically performed vaginally using a fine needle attached to and guided by a transvaginal ultrasound probe. The needle is ordinarily connected to fine Teflon® tubing and thence to an aspiration regulator controlled by a vacuum regulator. The aspirate is collected in test tubes or other appropriate vessels, containing medium. The medium may be used to preliminarily wash the needle and tubing, and other equipment used in the procedure. In some clinical settings, the medium may also be used with a specially adapted needle to flush the follicle and aid in removal of the oocyte. The medium, equipment used, and aspirate are maintained, so far as possible, at a temperature of about 37° C. If a bicarbonate buffer system is used in the medium, the procedure ordinarily is carried out in a gassed humidicrib or isolette which maintains an atmosphere containing 3% to 10% carbon dioxide ($CO_2$). In the absence of such atmospheric controls, the medium must contain a MOPS or HEPES buffering system.

Each phase of the oocyte retrieval procedure is typically conducted in an oocyte retrieval and handling medium. The oocyte retrieval and handling medium is typically an aqueous solution which is comprised of the ionic components, such as sodium, potassium, phosphate, magnesium, bicarbonate, and calcium, to maintain an osmotic environment that does not stress the oocyte, and a buffering system, preferably MOPS or HEPES, to maintain the pH of the medium within the physiological range of 7.3 to 7.4. Such an oocyte retrieval and handling medium is described in U.S. Pat. No. 6,838,235 B2. The teachings of U.S. Pat. No. 6,838,235 B2 are incorporated herein for the purpose of describing such an oocyte retrieval and handling medium.

In any case, the process of using the oocyte retrieval and handling medium normally involves washing any equipment that may come into contact with the oocyte during its removal from the ovary. The oocyte retrieval and handling medium may also be used to aspirate, flush and/or wash the oocyte during the removal and collection process. Following removal from the ovary, the oocyte may be washed with medium. Optionally, the oocyte may be stored in the medium for a period of time before being fertilized in the bioreactor in accordance with this invention.

In addition, it is contemplated that the medium may be used during other clinical or laboratory procedures where the oocyte is manipulated or handled, and also in procedures where the embryo is manipulated or handled, especially where these occur outside the isolette. Examples would include examination of the oocyte following retrieval from the mother, examination of the oocyte following the fertilization step, and examination of the embryo to determine whether it has developed the eight-cell stage. In each of these examples, the oocyte/embryo would be bathed in the medium as it is withdrawn by pipette from the culture dish or test tube, and would remain immersed in the medium while examined under a microscope or with other equipment. The illustrated implementation of the invention also contemplates that an alternative formulation of this medium, which is calcium and magnesium free, may be used during biopsy procedures.

Polycystic ovary syndrome (PCOS), also known as Stein-Leventhal syndrome, is characterized by menstrual irregularity and hirsutism and is a common cause of anovulatory infertility. In the case of polycystic ovary syndrome biochemical abnormalities include a high concentration of plasma luteinising hormone (LH) or a high LH/follicle stimulating hormone (FSH) ratio and high concentrations of androgens (testosterone and/or androstenedione and/or dehydroepiandrosterone (DHEA)). In any case, clinical manifestations of polycystic ovary syndrome include amenorrhea, hirsutism acanthosis *nigricans*, acne and obesity. Polycystic ovary syndrome appears to account for about 75% of anovulatory infertility. The chronic anovulation typical of polycystic ovary syndrome results in an increased number of atretic follicles (which become cysts) and increased interstitial tissue in the stroma of the ovaries. Under normal conditions, women produce a single dominant follicle that participates in a single ovulation each menstrual cycle. The process begins when a cohort of primordial follicles is recruited to initiate growth. Successive recruitment gives rise to the primary, secondary, tertiary and graafian follicles present in the ovaries. The ability to become a dominant follicle is not a characteristic shared by all follicles, and those that lack the property die by atresia due to increased androgens. In the human female, only about 400 of the original 7 million follicles survive atresia and give rise to dominant follicles.

In patients with polycystic ovary syndrome, the process of folliculogenesis does not proceed normally. The initial steps, recruitment and growth to the small graafian stages, are functioning in polycystic ovary syndrome, but the terminal step, the selection of dominant follicles that can ovulate, does not occur regularly. Viable follicles seldom develop beyond about the 6 mm stage. In some unexplained way, this condition leads to the accumulation of large numbers of small graafian follicles (commonly referred to as cysts) in which the theca interstitial cells (TIC) produce abnormally large amounts of androgen, but the granulosa cells (GC) fail to express the aromatase enzyme and aromatize the androgen substrate to estradiol. Consequently, a state of continued hyperandrogenism results. The problem is self-perpetuating in part because the atretic follicle becomes an androgenic follicle by a "default" mechanism: because of low aromatase activity in atretic follicles, androstenedione is preferentially metabolized to testosterone and thence to dihydrotestosterone within the ovary.

U.S. Pat. No. 6,352,997 B1 provides for a novel method of treating polycystic ovary syndrome. The method of U.S. Pat. No. 6,352,997 B1 is directed to a method of improving fertility and the response to in vitro fertilization by employing a 5-α-reductase type 1 inhibitor. U.S. Pat. No. 6,352,997 B1 also provides for a method of manufacture of a medicament useful for treating polycystic ovary syndrome and a method of manufacture of a medicament useful as an adjunct in in vitro fertilization. Some representative examples of therapeutically effective compounds delineated in this patent include: 4-aza-4,7-β-dimethyl-5-α-androstane-3,16-dione; 4-aza-4-methyl-5-α-androstan-3,16-dione; 3-oxo-4-aza-4-methyl-16-β-hydroxy-5-α-androstane; 3-oxo-4-aza-4-methyl-16-β-(benzylaminocarbonyloxy)-5-α-androstane; 3-oxo-4-aza-4-methyl-16-β-benzoylamino-5-α-androstane; 3-oxo-4-aza-4-methyl-16-β-methoxy-5-α-androstane; 3-oxo-4-aza-4-methyl-16-β-allyloxy-5-α-androstane; 3-oxo-4-aza-4-methyl-16-β-(n-propyloxy)-5-α-androstane; 3-oxo-4-aza-4-methyl-16-β-hydroxy-5-α-androstane; 3-oxo-4-aza-4-methyl-16-β-(phenoxy)-5-α-androstane; 3-oxo-4-aza-7-β-methyl-16-β-(phenoxy)-5-α-androst-1-ene; 3-oxo-4-aza-4-methyl-16-α-methoxy-5-α-androstane; 3-oxo-4-aza-4-methyl-16-β-(4-chlorophenoxy)-5-α-androstane; 3-oxo-4-aza-7-β-methyl-16-β-(4-chlorophenoxy)-5-α-androst-1-ene; 3-oxo-4-aza-7-β-methyl-16-β-(4-chlorophenoxy)-5-α-androstane; 3-oxo-4-aza-7-β-methyl-16-β-(3-chloro-4-methylphenoxy)-5-α-androstane; 3-oxo-4-aza-7-β-methyl-16-β-(4-methylphenoxy)-5-α-androstane; 3-oxo-4-aza-7-β-methyl-16-β-(4-methylphenoxy)-5-α-androst-1-ene; 3-oxo-4-aza-7-β-methyl-16-β-[4-(1-pyrrolyl)phenoxy]-5-α-androst-1-ene; 3-oxo-4-aza-4,7-β-dimethyl-16-α-hydroxy-5-β-androstane; 3-oxo-4-aza-4,7-β-dimethyl-16-β-methoxy-5-α-androstane; 3-oxo-4-aza-4,7-β-dimethyl-16-β-allyloxy-5-α-androstane; 3-oxo-4-aza-4,7-β-dimethyl-16-β-(3,3-dimethylallyloxy)-5-α-androstane; 3-oxo-4-aza-4,7-β-dimethyl-16-β-(n-propyloxy)-5-α-androstane; 3-oxo-4-aza-4,7-β-dimethyl-16-β-(iso-pentoxy)-5-α-androstane; 3-oxo-4-aza-4,16-α-dimethyl-16-β-hydroxy-α-androstane; 3-oxo-4-aza-4,7-β-dimethyl-16-β-ethyloxy-5-α-androstane; 3-oxo-4-aza-4,7-β-dimethyl-16-β-benzyloxy-5-α-androstane; 3-oxo-4-aza-4,7-β-dimethyl-16-α-hydroxy-5-α-androstane; 3-oxo-4-aza-4,7-β-dimethyl-16-β-methylthio-5-α-androstane; 3-oxo-4-aza-4,7-β-dimethyl-16-β-(n-propylthio)-5-α-androstane; 3-oxo-4-aza-4,7-β-dimethyl-16-β-fluoro-5-α-androstane; 3-oxo-4-aza-4,7-β-dimethyl-16-β-cyano-5-α-androstane; 3-oxo-4-aza-4-methyl-16-β-(1-hexyl)-5-α-androstane; 3-oxo-4-aza-4,7-β-dimethyl-16-β-(n-propyl)-5-α-androstane; 3-oxo-4-aza-4,7-β-dimethyl-16-β-benzyl-5-α-androstane; 3-oxo-4-aza-4,7-β-dimethyl-16-β-(4-chlorobenzyl)-5-α-androstane; 3-oxo-4-aza-4,16-α-dimethyl-16-β-methoxy-5-α-androstane; 3-oxo-4-aza-4,7-β-dimethyl-16-β-(4-cyanophenoxy)-5-α-androstane; 3-oxo-4-aza-4,7-β-dimethyl-16-β-(3-cyanophenoxy)-5-α-androstane; 3-oxo-4-aza-4,7-β-dimethyl-16-β-(4-nitrophenoxy)-5-α-androstane; 3-oxo-4-aza-4,7-β-dimethyl-16-β-(1-naphthyloxy)-5-α-androstane; 3-oxo-4-aza-4,7-β-dimethyl-16-β-(3-chloro-4-methylphenoxy)-5-α-androstane; 3-oxo-4-aza-4,7-β-dimethyl-16-β-(4-methylphenoxy)-5-α-androstane; 3-oxo-4-aza-4,7-β-dimethyl-16-β-(tert-butyloxy)-5-α-androstane; 3-oxo-4-aza-4,7-β-dimethyl-16-β-(3-methyl-1-butyloxy)-5-α-androstane; 3-oxo-4-aza-4,7-β-dimethyl-16-α-(n-propyloxy)-5-α-androstane; 3-oxo-4-aza-4,7-β-dimethyl-16-β-(4-trifluoromethylphenoxy)-5-α-androstane; 3-oxo-4-aza-4,7-β-dimethyl-16-β-(4-trifluoromethoxyphenoxy)-5-α-androstane; 3-oxo-4-aza-4,7-β-dimethyl-16-β-ethylthio-5-α-androstane; 3-oxo-4-aza-4,7-β-dimethyl-16-β-ethylsulfonyl-5-α-androstane; 3-oxo-4-aza-4,7-β-dimethyl-16-β-(4-methylsulfonylphenoxy)-5-α-androstane; 3-oxo-4-aza-4,7-β-dimethyl-16-β-[4-(4-tolylsulfonylamino)phenoxy]-5-α-androstane; 3-oxo-4-aza-4,7-β-dimethyl-16-β-(3-pyridyloxy)-5-α-androstane; 3-oxo-4-aza-4,7-β-dimethyl-16-β-[(4-phenyl) phenoxy]-5-α-androstane; 3-oxo-4-aza-4,7-β-dimethyl-16-β-(4-fluorophenoxy)-5-α-androstane; 3-oxo-4-aza-4,7-β-dimethyl-16-β-(2-pyrazinyloxy)-5-α-androstane; 3-oxo-4-aza-4,7-β-dimethyl-16-β-[4-(5-oxazolyl) phenoxy]-5-α-androstane; 3-oxo-4-aza-4,7-β-dimethyl-16-β-(2-pyrimidinyloxy)-5-α-androstane; 3-oxo-4-aza-4,7-β-dimethyl-16-β-[4-(1-pyrryl)phenoxy]-5-α-androstane; 3-oxo-4-aza-4,7-β-dimethyl-16-β-(4-aminophenoxy)-5-α-androstane; 3-oxo-4-aza-4,7-β-dimethyl-16-β-(4-acetylaminophenoxy)-5-α-androstane;

3-oxo-4-aza-4,7-β-dimethyl-16-β-(4-benzoylaminophenoxy)-5-α-androstane; 3-oxo-4-aza-4,7-β-dimethyl-16-β-(4-chlorophenoxy)-5-α-androsta ne; 3-oxo-4-aza-4,7-β-dimethyl-16-β-(phenoxy)-5-α-androstane; 3-oxo-4-aza-4,7-β-dimethyl-16-β-(2-chlorophenoxy)-5-α-androstane; 3-oxo-4-aza-4,7-β-dimethyl-16-β.-(3-chlorophenoxy)-5-α-androstane; 3-oxo-4-aza-4,7-β-dimethyl-16-β-(4-chlorophenoxy)-5-α-androst-1-ene; 3-oxo-4-aza-4,7-β-dimethyl-16-(4-chlorobenzylidene)-5-α-androstane; 3-oxo-4-aza-4,7-β-dimethyl-16-benzylidene-5-α-androstane; 3-oxo-4-aza-4,7-β-dimethyl-16-(4-methylbenzylidene)-5-α-androstane; 3-oxo-4-aza-4,7-β-dimethyl-16-(4-chlorobenzyl)-5-α-androstane; 3-oxo-4-aza-4,7-β-dimethyl-16-(4-methylbenzyl)-5-α-androstane; 3-oxo-4-aza-4,7-β-dimethyl-16-(3-pyridylmethyl)-5-α-androstane; 3-oxo-4-aza-4,7-β-dimethyl-16-α-methanesulfonyl-5-α-androstane; 3-oxo-4-aza-4,7-β-dimethyl-16-β-thiophenoxy-5-α-androstane; 3-oxo-4-aza-4,7-β-dimethyl-16-β-(4-chlorothiophenoxy)-5-α-androstane; 3-oxo-4-aza-4,7-β-dimethyl-16-β-(4-fluorothiophenoxy)-5-α-androstane; 3-oxo-4-aza-4,7-β-dimethyl-16-β-(4-methylthiophenoxy)-5-α-androstane; 3-oxo-4-aza-4,7-β-dimethyl-16-β-(4-methoxythiophenoxy)-5-α-androstane; 3-oxo-4-aza-4,7-β-dimethyl-16-β-phenylsulfinyl-5-α-androstane; 3-oxo-4-aza-4,7-β-dimethyl-16-β-phenylsulfonyl-5-α-androstane; 3-oxo-4-aza-4,7-β,16-α-trimethyl-16-β-(4-trifluoromethylphenoxy)-5-α-androstane; 3-oxo-4-aza-4,7-β,16-α-trimethyl-16-β-hydroxy-5-α-androstane; 3-oxo-4-aza-4,7-β,16-α-trimethyl-16-β-methoxy-5-α-androstane; 3-oxo-4-aza-4,7-β-dimethyl-16-β-(4-cyanophenoxy)-5-α-androstane; 3-oxo-4-aza-4,7-β-dimethyl-16-β-(3-cyanophenoxy)-5-α-androstane; 3-oxo-4-aza-4,7-β-dimethyl-16-β-(4-nitrophenoxy)-5-α-androstane; 3-oxo-4-aza-4,7-β-dimethyl-16-β-(1-naphthyloxy)-5-α-androstane; 3-oxo-4-aza-4,7-β-dimethyl-16-β-(3-chloro-4-methylphenoxy)-5-α-androstane; 3-oxo-4-aza-4,7-β-dimethyl-16-β-(4-methylphenoxy)-5-α-androstane; 3-oxo-4-aza-4,7-β-dimethyl-16-β-(4-trifluoromethylphenoxy)-5-α-androstane; 3-oxo-4-aza-4,7-β-dimethyl-16-β-(4-trifluoromethoxyphenoxy)-5-α-androstane; 3-oxo-4-aza-4,7-β-dimethyl-16-β-(4-methylsulfonylphenoxy)-5-α-androstane; 3-oxo-4-aza-4,7-β-dimethyl-16-β-[4-(4-tolylsulfonylamino) phenoxy]-5-α-androstane; 3-oxo-4-aza-4,7-β-dimethyl-16-β-[(4-phenyl) phenoxy)-5-α-androstane; 3-oxo-4-aza-4,7-β-dimethyl-16-β-(4-fluorophenoxy)-5-α-androstane; 3-oxo-4-aza-4,7-β-dimethyl-16-β-[4-(5-oxazolyl) phenoxy]-5-α-androstane; 3-oxo-4-aza-4,7-β-dimethyl-16-β-[4-(1-pyrryl) phenoxy]-5-α-androstane; 3-oxo-4-aza-4,7-β-dimethyl-16-β-(4-aminophenoxy)-5-α-androstane; 3-oxo-4-aza-4,7-β-dimethyl-16-β-(4-acetylaminophenoxy)-5-α-androstane; 3-oxo-4-aza-4,7-β-dimethyl-16-β-(4-benzoylaminophenoxy)-5-α-androstane; 3-oxo-4-aza-4,7-β-dimethyl-16-β-(4-chlorophenoxy)-5-α-androstane; 3-oxo-4-aza-4,7-β-dimethyl-16-β-(phenoxy)-5-α-androstane; 3-oxo-4-aza-4,7-β-dimethyl-16-β-(2-chlorophenoxy)-5-α-androstane; 3-oxo-4-aza-4,7-β-dimethyl-16-β-(3-chlorophenoxy)-5-α-androstane; and the pharmaceutically acceptable salts thereof. The teachings of U.S. Pat. No. 6,352,997 B1 are incorporated herein for the purpose of describing treatments for cystic ovary syndrome which can be employed in conjunction with the in vitro fertilization methods of this invention.

In the event the collected oocytes are immature, it is generally desirable to support and promote development of the oocyte in an oocyte maturation step. Oocyte maturation is typically used in the case of mothers who are unable to withstand the hormonal treatment ordinarily employed with in vitro fertilization procedures. Oocyte maturation generally involves treating the immature oocytes in vitro with the hormones follicle stimulating hormone (FSH) and human chorionic gonadotrophin (hCG) rather than injecting these hormones into the mother. The preferred medium is an aqueous solution that contains ionic constituents similar to those used in the oocyte retrieval and handling medium, at similar concentrations, although the magnesium level is increased and the calcium level decreased to maintain a 2:1 magnesium to calcium concentration. A buffer is included in the preferred medium to maintain a physiological pH. Because oocyte maturation ordinarily occurs in an incubator or isolette in which an elevated carbon dioxide ($CO_2$) atmosphere can be maintained, a bicarbonate buffering system is preferred. Other buffers may be used, provided they are compatible with the oocyte and other components of the medium.

The carbohydrates including glucose, lactate, and pyruvate are also included in the preferred maturation medium. Because of the presence and importance of cumulus cells that surround the developing oocyte, the glucose, lactate and pyruvate levels are adapted to the needs of the cumulus cells. Non-essential amino acids are preferably included in the medium to provide nutrients and avoid subjecting the oocyte to osmotic stress. Essential amino acids and vitamins may also be included to provide nutrients to the cumulus cells. The medium also contains HSA and hyaluronate, which act as a source of macromolecules. Insulin transferrin selenium (ITS), insulin-like growth factor (IGF), and epidermal growth factor (EGF) are included to support the function of cumulus cells, which, in turn, nourish and stimulate the oocyte. FSH and hCG are added to stimulate the cumulus and oocyte to undergo changes associated in vivo with ovulation. It should be noted that, when the maturation medium is prepared, ITS, IGF, EGF and FSH and hCG are preferably the last ingredients to be added.

In any case, the oocyte maturation medium employed in such an oocyte maturation step is ordinarily used to treat and mature the oocyte following the retrieval procedure, in which the oocyte is retrieved from the ovary using the oocyte retrieval and handling medium. The retrieval and handling medium and maturation medium have a very similar backbone of ionic constituents and amino acids and glutamine, such that as the oocyte is moved from one medium to another it experiences minimal ionic shock. The oocyte maturation step normally includes immersing the oocyte and surrounding cumulus cells in the maturation medium for a period of about 30 to about 48 hours, or until the oocyte is mature. The mature oocyte is than removed from the oocyte maturation medium for fertilization in the rotating bioreactor. An oocyte maturation medium that can be used in the practice of this invention is described in greater detail in U.S. Pat. No. 6,838,235 B2. The teachings of U.S. Pat. No. 6,838,235 B2 are incorporated herein by reference for the purpose of describing such an oocyte maturation medium.

In one embodiment of this invention, the oocyte maturation medium may be used in the oocyte retrieval process in place of the oocyte retrieval and. Additionally, a conventional culture medium, such as Ham's F-10 or medium TCM-199 with or without a HEPES buffer, may be employed for immature oocyte retrieval and handling before immersion of the oocyte in the maturation medium of the present invention. In any case, the oocytes that are collected will ordinarily be washed and subsequently pre-incubated in a first portion of a sperm preparation and fertilization medium to attain a higher rate of fertilization. This period of pre-incubation may last up to about 6 hours.

Current methods of in vitro fertilization employ the same medium for sperm preparation and fertilization as is used for embryo development. No attempt has been made to develop a separate medium for preparation of sperm that is also suitable for storage and support of the oocyte, for promoting the process of fertilization, and for supporting the zygotes formed when fertilization occurs. In many laboratories, the fertilization process is allowed to take place over an extended period which ranges from 2 to 3 hours to up to about 16 to 18 hours. During this time, the oocyte, sperm, and zygotes produced have significant nutritional needs. In addition, sperm function and fertilization tend to be encouraged when the surrounding fluid contains certain constituents.

A preferred sperm preparation and fertilization medium has virtually the same composition of ions and non-essential amino acids as the oocyte retrieval and handling medium. The fact that these media share a similar ionic and amino acid composition minimizes the stress experienced by the oocyte when it is removed from the retrieval and handling medium and placed in sperm preparation medium.

The sperm preparation medium will typically contain a higher concentration of sodium than the level found in the oocyte retrieval and handling medium. This elevated concentration of sodium promotes sperm function and fertilization, without causing undue osmotic stress to the oocyte. There is also a higher concentration of phosphate, as compared to the oocyte retrieval and handling medium. The glucose concentration of the sperm preparation and fertilization medium is elevated over that of the oocyte retrieval and handling medium, because glucose is the primary nutrient for sperm and cumulus cells around the egg. The lactate concentration of the present medium is lower than that found in the oocyte retrieval and handling medium, to compensate for the tendency of sperm cells and cumulus cells to give off lactic acid as a waste product. A buffering system is used to maintain the physiological pH, and because sperm preparation and fertilization largely occur within an incubator that can maintain an elevated carbon dioxide ($CO_2$) atmosphere, a bicarbonate buffer is preferred. Glutathione (not present in the oocyte retrieval and handling medium) is included, to assist in the process of sperm head decondensation. Alanyl-glutamine (present in the oocyte retrieval and handling medium) is omitted from the present medium because it can impair sperm function and reduce fertilization. The same is true of the chelating agent EDTA, which (as will be discussed later) is present in the embryo development media. HSA, the most abundant macromolecule in the Fallopian tube and uterus, is included to support sperm and embryo function. Hyaluronate, which promotes sperm motility, and works in tandem with HSA, is also included. Because sperm tends to contain high levels of bacteria, one or more antibiotic substances are also included with penicillin, streptomycin, and/or gentamycin being preferred antibiotics. A sperm preparation and fertilization medium that can be used in the practice of this invention is described in greater detail in U.S. Pat. No. 6,838,235 B2. The teachings of U.S. Pat. No. 6,838,235 B2 are incorporated herein by reference for the purpose of describing such a sperm preparation and fertilization medium.

U.S. Pat. No. 6,130,086 also discloses a medium composition for in vitro fertilization, and for use in culturing of ova or early embryos, the preparation or culture of sperm, and the pre-treatment of ova or sperm. This composition comprises, as its essential components, L-phenylalanine, L-tryptophan, L-lysine, L-threonine, L-valine, L-methionine, L-isoleucine, L-leucine, L-proline, glycine, L-alanine, L-tyrosine, L-histidine, L-arginine, L-taurine, L-aspartic acid, L-serine, L-asparagine, L-glutamic acid, L-glutamine and L-cystine, with it being understood that at least a part of the L-cystine can be replaced by L-cysteine. The teachings of U.S. Pat. No. 6,130,086 are incorporated herein by reference for the purpose of disclosing such an in vitro fertilization medium.

The sperm used in the practice of this invention will be collected from a male donor and prepared using standard procedures. Such a process contemplates that the sperm may be separately washed and stored in a second portion of the sperm preparation and fertilization medium to purge it of bacteria and any other contaminants that may be present. Sperm preparation may involve dilution of semen with the medium, centrifugation, and resuspension of the concentrated sperm in a new portion of medium. In the "swim up" method of sperm preparation, the medium containing sperm is centrifuged, the medium is drained off, and a new portion of medium is poured over the spun-down sperm pellet. The sperm is given a period to "swim up" into the fresh medium. That layer of fresh medium, containing the more motile sperm, is then poured off and centrifuged, and the process is repeated. In another aspect of the invention, the sperm preparation and fertilization medium may be used in one or more gradient separation procedures, such as the Percoll procedure. The present invention envisions that the sperm preparation and fertilization medium may be used as the medium in any of the sperm preparation procedures that may be used for in vitro fertilization.

The sperm is then examined and counted while in sperm preparation and fertilization medium, and a desired quantity is added to the portion of the medium which contains the oocyte in the bioreactor. The sperm and oocyte are then permitted to remain together in the sperm preparation and fertilization medium in the bioreactor for a period of up to 18 hours. The oocyte is typically exposed to the sperm in the bioreactor for a period of about 2 hours to about 16 hours with time periods which are within the range of 3 to 8 hours being more typical. Following the period of immersion in the medium with the sperm the oocytes will normally be removed and examined to determine whether fertilization has occurred. When removed for examination, the oocytes will continue to be bathed in the sperm preparation and fertilization medium if the examination can be conducted in an isolette. If not, then, as noted above, the oocyte retrieval and handling medium may be used for handling and examination of the oocytes.

In another embodiment of this invention, intracytoplasmic sperm injection (ICSI) can be used to fertilize the oocyte. Intracytoplasmic sperm injection is employed in circumstances where it is desired to accomplish fertilization by other than natural interaction between the sperm and the oocyte, such as where the sperm is unable to fertilize the oocyte due to a thickened zona pellucida surrounding the oocyte, or where the sperm is from a male-factor patient. In cases where the intracytoplasmic sperm injection technique is used, the cumulus cells are removed from the oocyte, and sperm is injected into the oocyte's interior using a glass pipette. In such cases, a single medium is normally used to bathe the oocyte and also to serve as a carrier for the sperm as it is transported by injection into the oocyte. The medium, accordingly, is preferably highly compatible with the interior and exterior of the oocyte. The ionic constituents in the preferred medium are similar to those found in the oocyte retrieval and handling medium, except that phosphate is omitted, to avoid metabolic and homeostatic stress, and the magnesium-to-calcium ratio is 2:1. This ratio of magnesium to calcium is felt to be highly beneficial to the oocyte. Because intracytoplasmic sperm injection is a clinical procedure performed outside the incubator, a buffering system that is effective in a normal atmosphere is used. MOPS and HEPES are accordingly preferred buffers for this medium. Because the cumulus cells have been removed from the oocyte, and the sperm is at the conclusion of its independent life, glucose, the main energy source for cumulus cells and sperm (but not the oocyte) is omitted from the medium. Pyruvate and lactate levels are increased, as these are a primary energy source for the oocyte. Only the non-essential amino acids most abundant in the oocyte, glycine, proline, serine and taurine, and glutamine (in the stable form alanyl-glutamine) are retained in the medium to avoid osmotic and pH stress and to nourish the oocyte. Preferably, the intracytoplasmic sperm injection medium also includes hyaluronate or polyvinylpyrrolidone (PVP), to immobilize or slow the sperm so that they may be captured in the intracytoplasmic sperm injection pipette. Moreover, an alternative formulation of the intracytoplasmic sperm injection medium includes hyaluronidase, which alternative formulation is used to pretreat the oocyte, to break down the hyaluronate gel holding the cumulus cells around the oocyte. This medium is referred to above as denuding medium, and lacks hyaluronate and PVP but includes hyaluronidase. Optionally, HSA may be included in the denuding medium in the preferred amount of 5 mM and the preferred range of 1.0-10 mM.

In the intracytoplasmic sperm injection process, sperm may be directly injected into the cytoplasm of the oocyte through a very fine pipette or needle. This process contemplates washing the sperm with a portion of the intracytoplasmic sperm injection medium containing hyaluronate and/or PVP, and then placing the sperm in the medium. The process further involves drawing a microvolume of the medium containing sperm into the pipette and then injecting the medium and sperm into the interior of the oocyte.

The oocyte may be bathed in another portion of the intracytoplasmic sperm injection medium during the intracytoplasmic sperm injection process. An alternative formulation of the intracytoplasmic sperm injection medium may be used, supplemented with hyaluronidase, for denuding pretreatment of the oocyte prior to the intracytoplasmic sperm injection process. Pretreatment involves immersing the oocyte in the intracytoplasmic sperm injection medium supplemented with hyaluronidase for a period until the oocyte becomes denuded of all or most of its surrounding cumulus cells. Following pretreatment, the oocyte is injected with sperm carried in a separate portion of medium using an intracytoplasmic sperm injection pipette.

After the intracytoplasmic sperm injection process is complete, it may be necessary to examine the oocyte to evaluate whether fertilization has been effective and the oocyte is intact and healthy. Examination may occur in the intracytoplasmic sperm injection medium bathing the oocyte, or may occur in the oocyte retrieval and handling medium as previously described.

After the oocyte has been fertilized in the bioreactor, by intracytoplasmic sperm injection, or by any other conventional means, the zygote is allowed to develop in an embryonic development step. This embryonic development step can be carried out in accordance with this invention in a rotating bioreactor or using a conventional technique. In any case, after the zygote is identified, it is normally washed and then cultured for a period of up to about 48 hours. During this time the embryo undergoes development from the one-cell to a blastocyst stage of a much larger size of more than 50, 100, 150, or 200 cells.

U.S. Pat. No. 6,838,235 B2 describes a medium that can be used in the embryonic development stage. More specifically this patent describes a medium that is reported to be optimized to support development of the early one-to-eight cell embryo. This preferred medium has a backbone of ionic constituents and non-essential amino acids that is similar to that found in the oocyte retrieval and handling medium. Unlike the oocyte retrieval and handling medium, this medium contains the component EDTA, which supports embryonic development and is believed to bind and disable toxins that might have a deleterious effect on the early embryo, and which also suppresses glycolysis. In addition, this medium includes HSA and hyaluronate, in concentrations that are thought to support early embryonic development. This formulation differs from the previously published medium G1 in several important respects. First, research has shown that an elevated phosphate concentration may not provide optimal conditions for growth of the developing embryo. Accordingly, the phosphate concentration has been decreased. Second, hyaluronate has been added to work in tandem with HSA. Third, alanyl-glutamine has been substituted for glutamine. A significant problem for embryo culture with amino acids is the natural decomposition of amino acids to ammonium, which decomposition is accelerated at higher temperatures such as the physiological temperature (37° C.) used in in vitro fertilization procedures. Ammonium can be toxic to embryos. Moreover, glutamine is especially prone to decomposition to ammonium within solution. Since embryos are generally cultured in during the early embryonic development stage for an extended period of up to about 48 hours, a significant quantity of ammonium can develop in the medium and be a significant inhibitor to embryo development. Accordingly, the use of alanyl-glutamine provides substantial advantages; it is a particularly stable form of glutamine and is not prone to breaking down in solution. Also, the concentration of alanyl-glutamine should optimally be reduced to of level of about 0.5 mM. These three modifications make a significantly improvement over conventional G1 medium for early embryonic development.

U.S. Pat. No. 6,838,235 B2 also described a medium formulation that is specifically formulated for the development of embryos from the eight-cell to the blastocyst stage (approximately 100 cells or more). The backbone of ionic constituents and non-essential amino acids preferably found in this medium are essentially the same as used with medium G1, except that the concentration of alanyl-glutamine is increased. Taurine is omitted because its benefits to the embryo appear to be confined to the period prior to compaction. Glucose, lactate and pyruvate are included as carbohydrates, except that the concentration of glucose is increased, while lactate and pyruvate are decreased. This modification in carbohydrate levels is in response to the increasing ability of the developing embryo to metabolize glucose as an energy source, and reflects also the observed composition of the female reproductive tract. Eagle's essential amino acids are included in the medium because they are necessary to stimulate the growth of the inner-cell mass of the blastocyst. Vitamins are added as a group because in animal studies they tend to facilitate the function of the blastocyst, including fluid accumulation in the cavity of the blastocyst. Importantly, this medium lacks EDTA. The teachings of U.S. Pat. No. 6,838,235 B2 are incorporated by reference herein for the purpose of describing formulations for utilization during the embryonic development stage (during early development and subsequently for later development to a blastocyst).

Once the embryo reaches the blastocyst stage, and assuming that the embryo is judged on examination to be viable, it is removed from the embryonic development medium and prepared for transfer into the uterus. In some cases medium from the bioreactor may, optionally, be used for embryo transfer as well. Examination of the embryo may occur in the medium or in the oocyte retrieval and handling medium. The embryo transfer medium can serve as a carrier for the embryo for implantation into the uterus of the female recipient. The embryo will generally be bathed in the transfer medium and the medium containing the embryo will be drawn into a transfer catheter. The catheter will then be inserted into the uterus of the recipient female which will normally be guided by an ultrasound probe, and then the medium containing the embryo will be injected into the uterus to achieve pregnancy.

A number of rotating bioreactor systems, components, and methods of operating said bioreactors are discloses in U.S. Pat. Nos. 4,988,623, 5,026,650, 5,153,131, and 5,155,034. One type of bioreactor which is described is referred to as a slow turning lateral vessel (STLV) and the other is a rotating wall perfused vessel (RWPV). In any case, the teachings of U.S. Pat. Nos. 4,988,623, 5,026,650, 5,153,131, and 5,155,034 are incorporated herein by reference for the purpose of disclosing such rotating tubular bioreactor systems, components, and methods of operating said bioreactors that can be used in various embodiments of practicing the subject invention.

U.S. Pat. No. 5,026,650 to Ray P. Schwarz et al. discloses a basic bioreactor that can be employed in the practice of this invention. This bioreactor includes (a) an elongated tubular culture vessel; (b) end caps enclosing the ends of said culture vessel; (c) a shaft co-axially disposed in said culture vessel and extending between said end caps; (d) a tubular membrane disposed over said shaft between said end caps and sealed with respect to said shaft for defining an annular passageway between said membrane and said shaft and for defining an annular culture chamber between said membrane and the inner wall of said culture vessel; (e) an oxygenation means for admitting an oxygen containing gas under pressure at one end of said annular passageway defined by said membrane and for exiting the gas at the other end of said annular passageway defined by said membrane, said membrane being oxygen permeable for exchange of component gases with said culture chamber; (f) a means for admitting a fluid culture medium into said culture chamber which is capable of completely filling said culture chamber with the fluid culture medium; and (g) a means for rotating said culture vessel, said shaft and said membrane about a horizontal axis at a rate sufficient to suspend the beads in a fluid motion while admitting oxygen about the circumference of the membrane on said shaft.

Such a bioreactor will typically include a horizontally disposed cylinder with end caps defines a cell culture vessel which is rotatable about an approximate horizontal axis. One of the end caps is attached to a motor drive for rotating the cylinder about its centerline horizontal axis. A centrally located, coaxial, internal cylindrical support shaft is attached to the end caps and supports an annular tube of the gas permeable membrane. In one of the end caps is an access passageway to access an oxygen containing gas through the shaft to the interior of the annular membrane at one end of the membrane. At the other end cap is an exit passageway to exit the gas through the shaft from the interior of the membrane at the other end of the membrane. The exit end cap also has separate controlled access entry ports to the interior of the cell culture vessel for sampling, changing or adding fluid and/or other materials. The system will normally be sterilized and liquid medium will completely fill the culture vessel. An oxygen containing gas is admitted to the interior of the permeable membrane which prevents air bubbles from being introduced into the medium. The cylinder is rotated at a low speed within an incubator so that the circular motion of the fluid medium uniformly suspends the particles and species of biological material throughout the cylinder.

The system thus involves rotating the fluid medium having zero head space having a first density about a nearly rotational horizontal axis where discrete suspension materials disposed in the fluid medium have a same or different density from the density of the fluid medium. The rotation of the fluid medium is controlled to place the discrete suspension materials in suspension at spatial locations in the fluid nutrient medium out of an interference relationship with one another by virtue of the rotation and so that they are not subjected to fluid shear forces generated by velocity gradients at the boundary layer at the vessel wall while rotating the fluid a medium gas is allowed to exchange across a diffusion membrane to the fluid nutrient medium.

Figure 1:
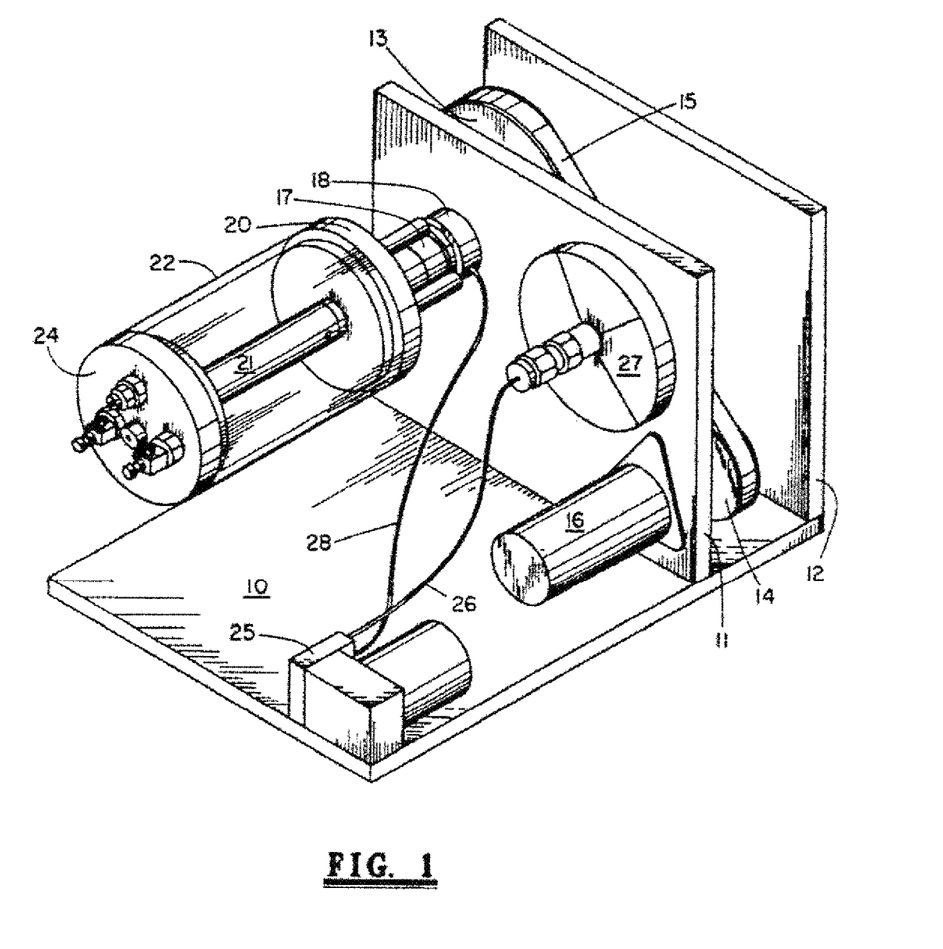

FIG. 1 illustrates a conventional bioreactor that can be utilized in accordance with this invention. A frame means 10 has vertical and spaced apart plates 11 and 12 which support a motor pulley 14 and a housing pulley 13 where the pulleys 13 and 14 are connected by a belt drive 15. The motor pulley 14 is coupled to a motor 16 which can be controlled to provide a desired drive speed (rate of angular rate of rotation). The housing pulley 13 is connected to a drive shaft 17 which extends through a rotative coupling 18 to an inlet end cap 20. The inlet end cap 20 is attached to a central assembly 21 and to a tubular outer culture cylinder 22. At the other end of the central assembly 21 and the culture cylinder 22 is an outlet end cap 24. An air pump 25 on the frame means 10 is connected by input tubing 26 to a filter 27. An output tubing 28 from the pump 25 couples to the rotative coupling 18 where the air input is coupled from a stationary annular collar to an internal passageway in the rotating drive shaft 17.

Figure 2:
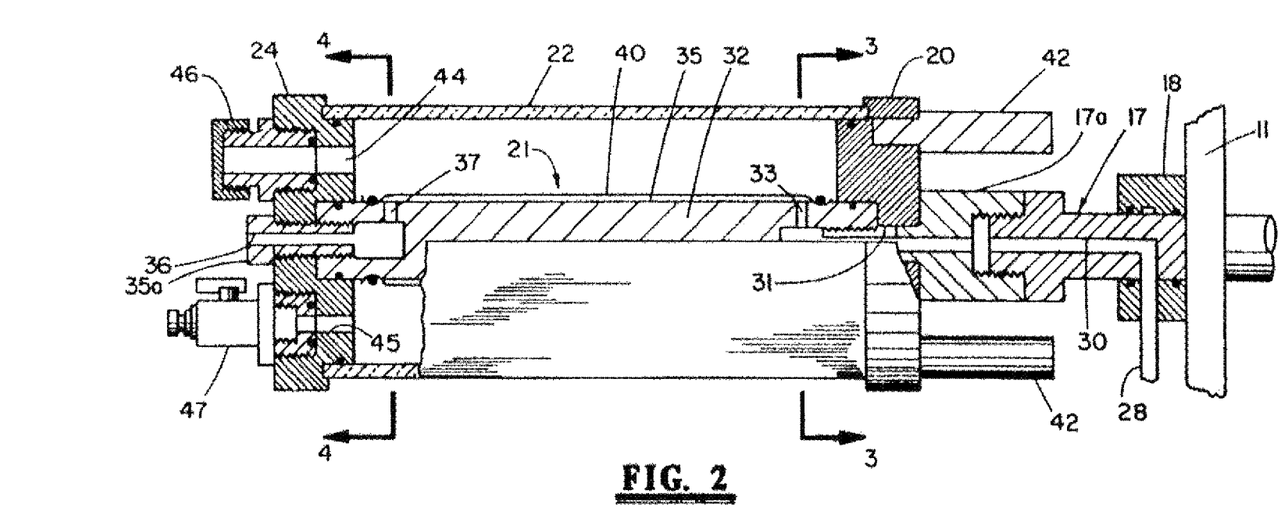
Figure 3:
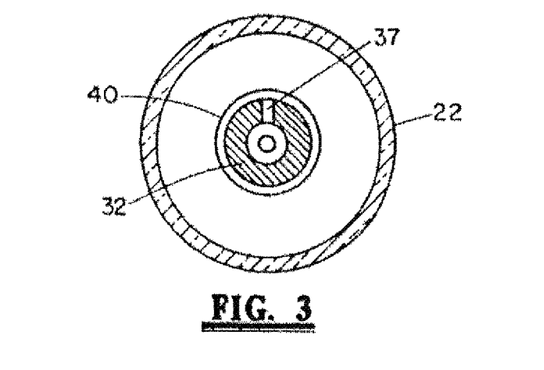
Figure 4:
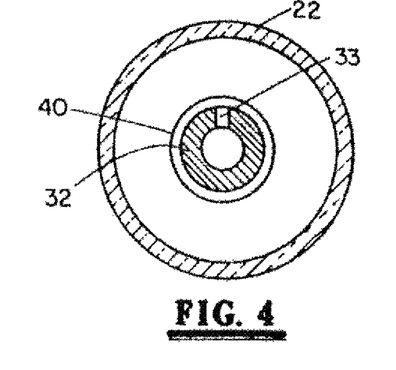

FIG. 2 illustrates the bioreactor where the rotative coupling 18 receives the output tubing 28 and the drive shaft 17 has a central air inlet passageway 30 for the passage of air. The drive shaft 17 is attached to a coupling shaft 17a which extends through a central opening 31 in the inlet end cap 20. The coupling shaft 17a is attached to a cylindrically shaped, central support member 32 by threading. The central passageway 30 extends inwardly through the shafts 17 and 17a to a transverse opening 33 which couples the air inlet passageway 30 to the exterior surface 35 of the central support member 32. The central support member 32 is sealingly received in a counterbore in the inlet end cap 20 and at its opposite end, the support member 32 is sealingly received in a counterbore of the outlet end cap 24. A tubular outlet member 35a is attached by threading through a bore in the outlet end cap 24 to a blind bore in the support member 32 and an air exit passageway 36 in the outlet coupling is connected by a transverse opening 37 to the exterior surface 35 of the central support member 32. A tubular oxygen permeable membrane 40 is disposed over the central support member 32 and has its ends extending over the openings 33 and 37 in the central support member 32 so that the membrane 40 can be sealingly attached to the central support member 32 by O-rings or the like. Thus an air passageway is provided for an input of air through the passageway 30 and the transverse opening 33, through the annular space between the inner wall of the membrane 40 and the outer wall of the central support member 32 to the exit transverse opening 37 and to the exit passageway 36. The membrane 40 may be made of silicone rubber which operates under air pressure to permit oxygen to permeate through the wall of the membrane into the annulus of fluid medium surrounding the membrane and carbon dioxide to diffuse in the opposite direction.

Coaxially disposed about the central support shaft 32 is a tubular outer cylinder 22 which can be glass. The cylinder 22 is sealing received on the end caps 20 and 24 and defines an annular culture chamber between the inner wall of the cylinder 22 and the outer surface of the membrane 40. On the inlet end cap 20 are circumferentially spaced apart cylindrical members 42. When the coupling shaft 17a is detached from the shaft 17, the members 42 provide a base for standing the cylinder 22 upright or in a vertical position for sampling, changing or adding fluids to the system. In the outlet end cap 24, there are two or more access ports 44 and 45 each having closure means 46. A hypodermic needle with fluid medium can be inserted through one access port to inject fluid when withdrawing fluid from the other port. In this regard samples or media can be withdrawn without forming an air space, thereby preserving the zero head space.

The present invention thus involves the central cylindrical core which is a source of oxygenation through the cylindrical membrane and the membrane and outer wall of the vessel are rotated about a horizontal axis. This involves a type of clinostat principal, i.e. a principal that fluid rotated about a horizontal or nearly horizontal axis can effectively suspend particles in the fluid independent of the effects of gravity. The rotational speed of the cylinder 22 effectively eliminates the velocity gradient at the boundary layer between the fluid and the cylinder wall. Thus, shear effects caused with a rotating fluid and stationary wall are significantly reduced or eliminated.

Since sperm cells and oocyte have similar rates of sedimentation it is generally advantageous to conduct the fertilization in the bioreactor under conditions of hyper-gravity to facilitate and enhance inter-galactic interaction between the sperm and the oocyte. The use of hyper-gravity is particularly advantageous in cases where a limited number of sperm cells are available to fertilize the oocyte. In any case, the use of hyper-gravity generally enhances the probability of fertilization by increasing the level of inter-galactic motion within the bioreactor. The level hyper-gravity desired is normally generated by centrifugal action and is typically within the range of 1 g to 5000 g. In such cases, the bioreactor will typically be operated under a level of hyper-gravity which is within the range of 20 g to 1000 g and more typically which is within the range of 50 g to 500 g.

It is normally preferred for the oocyte to be cultured in the bioreactor on a substrate. A wide variety of materials can be utilized as the substrate. Polyethylene glycol (PEG) is a representative example of a preferred material of which the substrate can be comprised. Polyethylene glycol is also known as polyethylene oxide (PEO) or polyoxyethylene (POE), has been assigned the CAS Number 25322-68-3, and is of the formula: $H-(O-CH_2-CH_2)_n-OH$, wherein n represents an integer of about 10 to about 20,000 and which is more typically within the range of 20 to 10,000. The size of the substrate on which oocyte is cultured can be adjusted to attain a desired sedimentation rate. For instance, increasing the size of the substrate on which the oocyte is cultured normally reduces the rate of sedimentation in the case of substrates of relatively low density, such as substrates which are comprised of polyethylene glycol. Accordingly, the sedimentation rate difference between sperm cells and oocyte can be increased by culturing the oocyte on a substrate. In doing so the probability of successful fertilization is enhanced.

Figure 5:
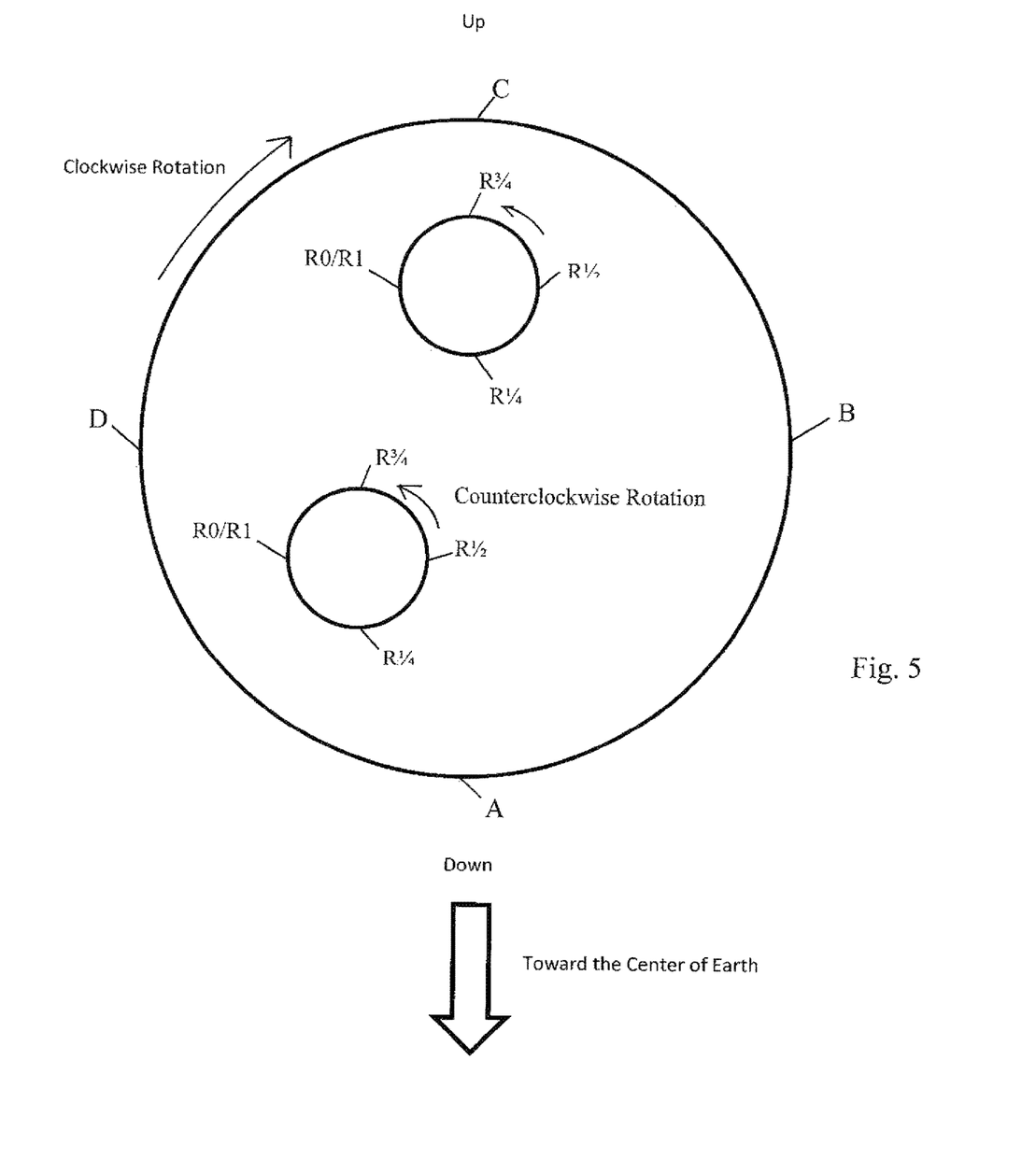

Rotating tubular bioreactors which are operated on Earth will, of course, fall under the influence of the gravitational attraction generated by Earth's mass. The force of gravity on the surface of Earth is approximately 9.8 $m/s^2$ or 32.2 $feet/second^2$. In any case, species (biological materials, such as cells, cell cultures, sperm, oocyte, as the like) within a bioreactor will be attracted downwardly (toward the center of the Earth) by the force of gravity. FIG. 5 is a cross-sectional view of a horizontally elongated rotating tubular bioreactor 1 having an outside wall 2 wherein the tubular bioreactor 1 contains two species having the same sedimentation rate. As the tubular bioreactor 1 rotates in a clockwise direction the species within the reactor are pulled downwardly by the force of gravity (assuming that the species are denser than the liquid medium within the reactor). If the species are less dense than liquid medium within the tubular bioreactor 1 then they will float upwardly as a result of their buoyancy.

For purposes of illustration, points A, B, C, and D have been identified on the outer wall 2 of the tubular bioreactor 1. At an arbitrary starting time, R0 (zero rotations) it will be assumed that point A on the outside wall 2 of the bioreactor 1 is oriented downwardly (toward the center of Earth) and the point C is oriented upwardly (away from the center of Earth). As the tubular bioreactor 1 rotates at a constant speed (angular rate of rotation) the species within the bioreactor also rotate within the bioreactor in an essentially circular or elliptical pattern in counterclockwise direction. As can be seen from FIG. 5, the rotational pattern of the first species S1 and the rotational pattern of the second species S2 are essentially the same.

After the tubular bioreactor has completed ¼ of a revolution (when point B is down) the first species and the second species will be at the points identified as R1/4 relative to the outside wall 2 of the tubular reactor 1 (as would be observed from a camera which was mounted to and which rotated with the outside wall 2 of the tubular reactor 1). After the tubular bioreactor has completed ½ of a revolution (when point C is down) the first species and the second species will be at the points identified as R1/2; after the tubular bioreactor has completed ¾ of a revolution (when point D is down) the first species and the second species will be at the points identified as R3/4; and after the tubular bioreactor has completed one full revolution (when point A is again down) the first species and the second species will be at the points identified as R0/R1. As the tubular reactor continues to rotate at a constant rate of angular rate of rotation in subsequent revolutions the first and second species will continue to follow essentially the same paths as they followed in the first revolution.

Figure 6:
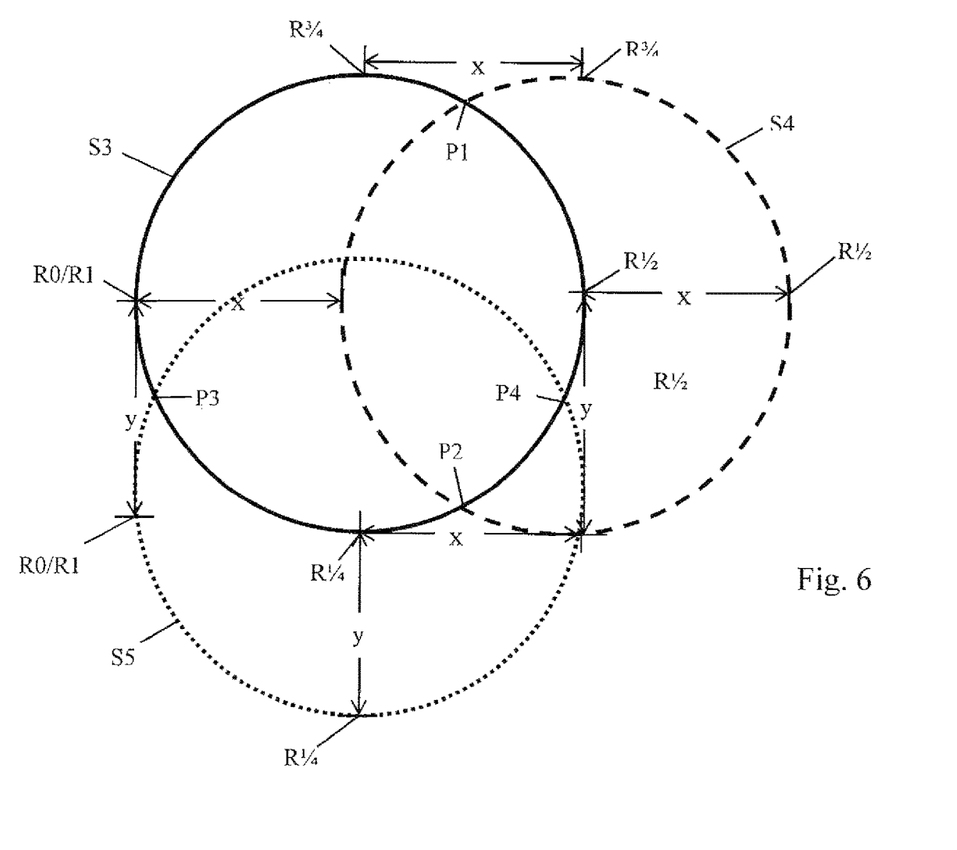

As a tubular bioreactor operated at a constant angular rate of rotation all species having the same sedimentation rate will rotate in the bioreactor in essentially the same pattern at the same rate. Accordingly, species having the same sedimentation rate will not come in contact with each other (collide) by virtue motion caused by the rotation of the bioreactor. In fact, FIG. 6 shows that all species having the same sedimentation rate will remain separated at a constant distance as they revolve in similar patterns. As can be seen, species S3 remains separated from species S4 by a horizontal distance x as the species rotate through revolutions of the tubular bioreactor. By the same token, S3 remains separated from species S5 by a vertical distance y as the species rotate through revolutions of the tubular bioreactor. Accordingly, species having the same sedimentation rate will remain separated from each other as the tubular bioreactor rotates. It should also be noted that species S3 and species S4 arrive at the points where their orbits intersect P1 and P2 at different times and accordingly do not come together. More specifically, S3 arrives at P1 after the bioreactor has rotated less than ¾ of a revolution while S4 only arrives at P1 after the bioreactor has rotated well over ¾ of a revolution. It should be further noted that S4 arrives at P2 after the bioreactor has rotated less than ¼ of a revolution while S3 arrives at P2 well after the bioreactor has completed ¼ of a revolution. Species S3 also arrives at the points where its orbit intersects the orbit of S5 at different times then does S5 and accordingly S3 does not come into contact with S5 either. As can be seen from FIG. 6, S3 arrives at P3 after only about 1/16 of a revolution of the bioreactor with S5 arriving at P3 after the bioreactor has completed approximately 15/16 of a revolution. FIG. 6 also shows that S3 arrives at P4 after the bioreactor has completed less than ½ of a revolution with S5 arriving at point P4 only after the bioreactor has completed well more than ½ of a revolution. It is also clear from FIG. 6 than S4 does not come into contact with S5 at the points where their orbits intersect.

Figure 7:
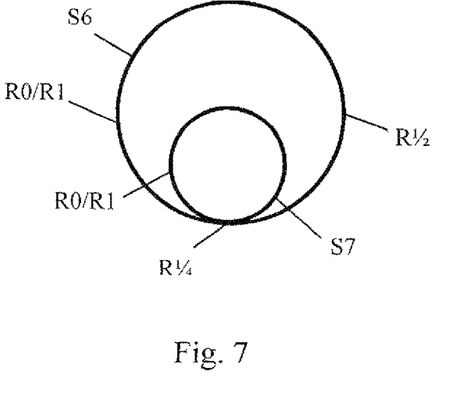
Figure 8:
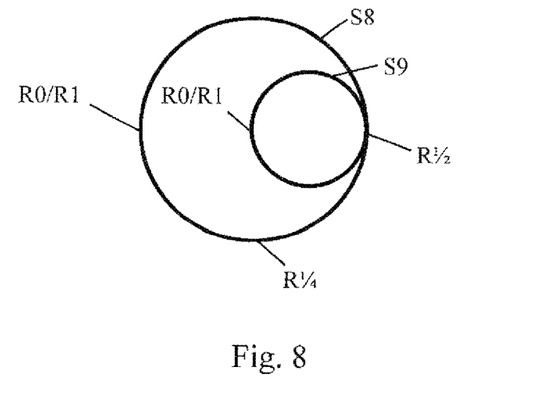

In FIG. 7 species S6 has a sedimentation rate which is twice as great as the sedimentation rate of species S7 and accordingly sings twice as far as the tubular bioreactor rotates. Accordingly, in the scenario depicted in FIG. 7 species S6 will come in contact with species S7 after ¼ of a revolution of the tubular bioreactor. In FIG. 8 species S8 is depicted as having a sedimentation rate which is twice as great as the sedimentation rate of species S9 and accordingly sings twice as far as the tubular bioreactor rotates. Accordingly, in the scenario depicted in FIG. 8 species S8 will come in contact with species S9 after ½ of a revolution of the tubular bioreactor. In any case, FIG. 7 and FIG. 8 illustrate the fact that species having different sedimentation rates can come in contact with each other in a tubular bioreactor which is operated at a constant speed (angular rate of rotation). However, only a limited number of species that are oriented in a manner whereby they will come into contact with each other during the first revolution of the bioreactor will make contact. In other words, as the bioreactor continues to rotate additional interaction with other species will not occur on subsequent revolutions.

The number of interactions between different species having different sedimentation rates can be greatly enhanced by inducing intergalactic motion. This can be accomplished by modulating the angular rate of rotation of the bioreactor. The angular rate of rotation can be modulated in a predetermined manner or in a random manner. In most cases, the angular rate of rotation will be modulated sinusoidal manner or as a function of square waves. For instance, the rate of angular rotation can be slowly increased and decreased in a sinusoidal manner from a minimum speed to a maximum speed as the bioreactor is operated. For instance, the rate of angular rotation can be increased from a minimum speed to a maximum speed over a period of about 2 minutes to about 60 minutes and then decreased back to a minimum speed over a similar time period. This time period for modulating the rate of angular rotation between a minimum speed and a maximum speed will more typically be within the range of about 5 minutes to about 50 minutes (within the range of 10 minutes to 20 minutes, 20 minutes to 30 minutes, 30 minutes to 40 minutes, or 40 minutes to 50 minutes). In the alternative, the rate of angular rotation can be incrementally increased and decreased as the bioreactor is operated. For instance, the speed of angular rotation can be modulated as a function of square waves by incrementally and slowly increasing the speed after each revolution from a minimum speed to a maximum speed and then slowly and incrementally decreasing the rate of angular rotation after each rotation from the maximum speed to the minimum speed.

Figure 9A:
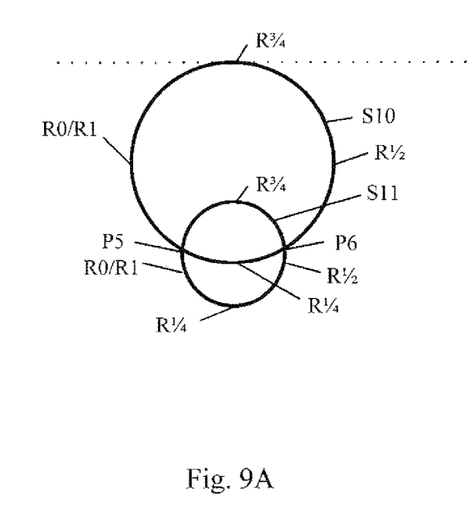
Figure 9B:
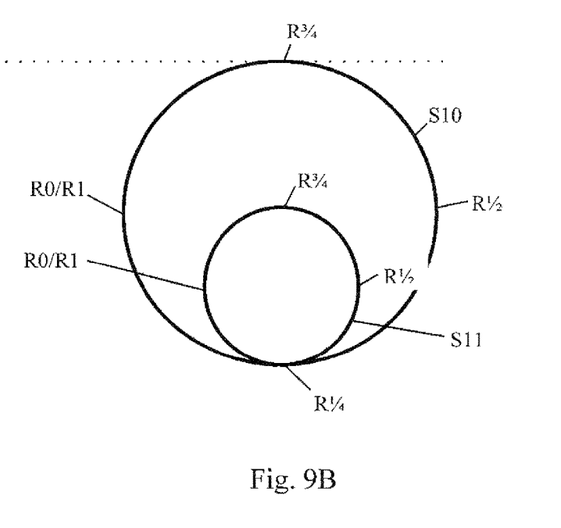

FIG. 9A illustrates a scenario where species S10 which has a sedimentation rate that is twice a great as S11 and in which S10 and S11 do not come into contact as the bioreactor rotates. At the two points where the paths of S10 and S11 cross S10 and S11 do reach these points at the same time in the rotation cycle of the bioreactor. More specifically, S10 reaches point P5 within the first quarter (¼) of a rotation of the bioreactor while S11 does not reach point P5 until the first revolution of the bioreactor is almost completed (between ¾ of a rotation and a full rotation). Also, S10 reaches point P6 shortly after completing the first quarter (¼) of a rotation of the bioreactor while S11 does not reach point P6 until more than half of a revolution of the bioreactor is completed. Accordingly, species S10 and species S11 cannot ever come into contact with each other at the rate of angular rotation depicted in FIG. 9A. However, species S10 and species S11 will come in contact with each other if the rate of angular rotation utilized in FIG. 9A is reduced by 50% which will double the downward travel of species S10 and species S11 in the bioreactor. In this scenario, as illustrated in FIG. 9B, S10 and S11 will meet after one-quarter of a rotation of the bioreactor. Accordingly, by modulating the angular rate of rotation of the bioreactor intergalactic motion can be enhanced which will exponentially increase interaction between species having different sedimentation rates.

Figure 10A:
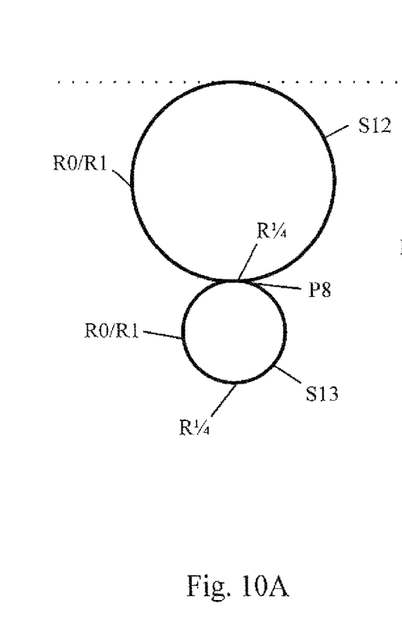
Figure 10B:
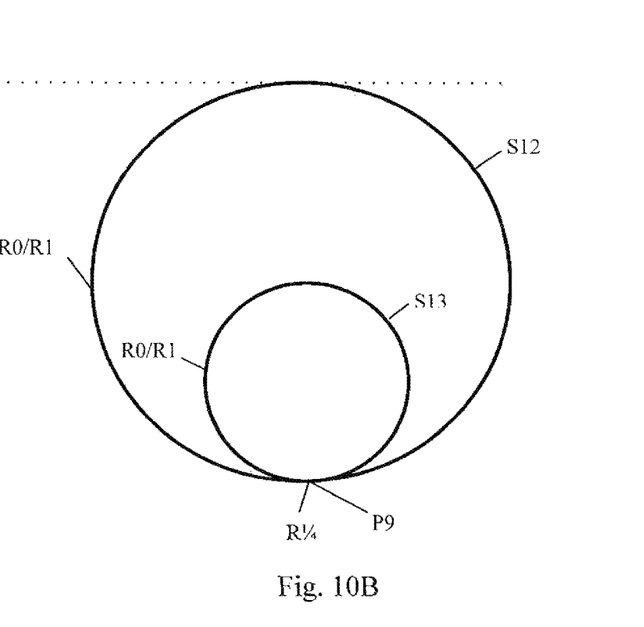

FIG. 10A illustrates a scenario where species S12 has a sedimentation rate which is twice as great as the sedimentation rate of S13. In this scenario the orbitals of species S12 and species S13 intersect at point P8. However, S12 reaches P8 after ¼ of a revolution of the bioreactor with S13 not arriving at that P8 until ¾ of a revolution of the bioreactor. Accordingly, S12 never comes in contact with S13. Intergalactic motion can be used to cause S12 and S13 to come into contact by reducing the angular rate of rotation of the bioreactor by 50%. The doubles the size of the essentially circular orbital paths taken by both S12 and S13 which now come into contact at point P9.

While certain representative embodiments and details have been shown for the purpose of illustrating the subject invention, it will be apparent to those skilled in this art that various changes and modifications can be made therein without departing from the scope of the subject invention.

What is claimed is:

1. A method for in vitro fertilization of an oocyte which comprises fertilizing the oocyte with a sperm cell to produce a zygote, wherein the fertilization is conducted in a rotating bioreactor containing an in vitro fertilization medium, wherein the bioreactor is a horizontally elongated cylinder having a centerline horizontal axis, wherein the horizontally elongated cylinder is rotatable about the centerline horizontal axis, wherein the horizontally elongated cylinder is attached to a motor drive for rotating the cylinder about its centerline horizontal axis, wherein the horizontally elongated cylinder is rotated about the centerline horizontal axis, wherein the in vitro fertilization medium completely fills the rotating bioreactor, wherein the in vitro fertilization medium is not subjected to fluid shear forces, wherein the bioreactor is operated under conditions of hyper-gravity, and wherein the level of hyper-gravity generated is within the range of 1.05 g to 5000 g.

2. The method as specified in claim 1 which further comprises culturing the zygote into a blastocyst stage embryo in the rotating bioreactor under hyper-gravity.

3. The method as specified in claim 2 which further comprises recovering the blastocyst stage embryo and subsequently implanting the blastocyst stage embryo into a uterus of a recipient female.

4. The method as specified in claim 3 wherein the female is a human female.

5. The method as specified in claim 2 wherein the zygote is cultured in the rotating bioreactor into a blastocyst stage embryo which is comprised of more than 50 cells.

6. The method as specified in claim 2 wherein the zygote is cultured in the rotating bioreactor into a blastocyst stage embryo which is comprised of more than 100 cells.

7. The method as specified in claim 2 wherein the zygote is cultured in the rotating bioreactor into a blastocyst stage embryo which is comprised of more than 150 cells.

8. The method as specified in claim 2 wherein the zygote is cultured in the rotating bioreactor into a blastocyst stage embryo which is comprised of more than 200 cells.

9. The method as specified in claim 1 wherein the angular rate of rotation of the rotating bioreactor is modulated by increasing the rate of angular rotation from a minimum speed to a maximum speed over a period of 2 minutes to 60 minutes and then decreasing the speed of angular rotation back to the minimum speed over a period of 2 minutes to 60 minutes with the bioreactor being rotated at a speed which is within the range of 5 RPM to 100 RPM.

10. The method as specified in claim 9 wherein the angular rate of rotation is modulated in a predetermined manner.

11. The method as specified in claim 10 wherein the angular rate of rotation is modulated sinusoidally.

12. The method as specified in claim 10 wherein the angular rate of rotation is modulated as a function of square waves.

13. The method as specified in claim 9 wherein the angular rate of rotation is modulated in a random manner.

14. The method of claim 1 wherein the oocyte is collected from a female donor, wherein the sperm is collected from a male donor, wherein the zygote is cultured into a blastocyst stage embryo, and wherein the blastocyst stage embryo is implanted into a uterus of a recipient female.

15. The method as specified in claim 1 wherein the oocyte is fertilized in the bioreactor in an aqueous fertilization medium which is an in vitro fertilization medium which is comprised of water and amino acids.

16. The method as specified in claim 1 wherein the conditions of hyper-gravity are generated by centrifugal action.

17. The method as specified in claim 1 wherein the level of hyper-gravity generated is within the range of 2 g to 1000 g.

18. The method as specified in claim 1 wherein the level of hyper-gravity generated is within the range of 50 g to 500 g.

* * * * *